(12) United States Patent
Laird et al.

(10) Patent No.: US 7,004,942 B2
(45) Date of Patent: Feb. 28, 2006

(54) RIBBED ELECTRODES AND METHODS FOR THEIR USE

(75) Inventors: Robert J. Laird, Richmond, CA (US); Frank W. Ingle, Palo Alto, CA (US); Garry L. Carter, Pleasanton, CA (US); Timothy G. Dietz, Fremont, CA (US)

(73) Assignee: Solarant Medical, Inc., Livermore, CA (US)

( * ) Notice: Subject to any disclaimer, the term of this patent is extended or adjusted under 35 U.S.C. 154(b) by 0 days.

(21) Appl. No.: 10/351,245

(22) Filed: Jan. 23, 2003

(65) Prior Publication Data

US 2003/0135249 A1 Jul. 17, 2003

Related U.S. Application Data

(63) Continuation of application No. 09/925,501, filed on Oct. 23, 2000, now Pat. No. 6,533,780, which is a continuation of application No. 09/229,508, filed on Jan. 12, 1999, now Pat. No. 6,283,987.

(60) Provisional application No. 60/071,324, filed on Jan. 14, 1998.

(51) Int. Cl.
*A61B 18/18* (2006.01)
(52) U.S. Cl. .............................. 606/50; 606/23; 606/28; 606/41; 607/96; 607/101
(58) Field of Classification Search .......... 607/96–107, 607/152–156; 128/894–856; 600/9–13, 600/33–52, 373; 606/33–52, 20–31
See application file for complete search history.

(56) References Cited

U.S. PATENT DOCUMENTS

| 373,399 A | 11/1887 | Hamilton |
| 728,883 A | 5/1903 | Downes |
| 3,575,158 A | 4/1971 | Summers |
| 3,749,098 A | 7/1973 | De Bennetot |
| 3,924,631 A | 12/1975 | Mancusi, Jr. |
| 3,926,175 A | 12/1975 | Allen et al. |
| 3,939,821 A | 2/1976 | Roth |
| 4,311,145 A | 1/1982 | Esty et al. |
| 4,409,453 A | 10/1983 | Smith |
| 4,453,536 A | 6/1984 | Abild |
| 4,679,561 A * | 7/1987 | Doss ........................... 607/99 |

(Continued)

FOREIGN PATENT DOCUMENTS

WO   WO 93/07815   4/1993

(Continued)

OTHER PUBLICATIONS

Hayes et al., "Prediction of Transient Temperature Fields and Cumulative Tissue Destruction for Radio Frequency Heating of a Tumor" *Med. Phys.* 12:6 (Nov./Dec. 1985) pp. 684-692.

*Primary Examiner*—A. Farah
(74) *Attorney, Agent, or Firm*—Townsend & Townsend & Crew LLP; Mark D. Barrish

(57) ABSTRACT

The invention provides improved devices, methods, and systems for shrinking of collagenous tissues, particularly for treating urinary incontinence in a noninvasive manner by directing energy to a patient's own support tissues. This energy gently heats fascia and other collagenous support tissues, causing them to contract. The energy will preferably be applied between a pair of large plate electrodes having cooled flat electrode surfaces separated by an insulating rib or film. Such cooled plate electrodes are capable of directing electrical energy through an intermediate tissue and into fascia while the cooled electrode surface prevents injury to the intermediate tissue.

18 Claims, 14 Drawing Sheets

U.S. PATENT DOCUMENTS

| | | |
|---|---|---|
| 4,686,962 A | 8/1987 | Haber |
| 4,765,331 A | 8/1988 | Petruzzi et al. |
| 4,773,393 A | 9/1988 | Haber et al. |
| 4,776,344 A | 10/1988 | Shirasaki et al. |
| 4,802,479 A | 2/1989 | Haber et al. |
| 4,807,620 A | 2/1989 | Strul et al. |
| 4,832,680 A | 5/1989 | Haber et al. |
| 4,994,019 A | 2/1991 | Fernandez et al. |
| 5,003,991 A | 4/1991 | Takayama et al. |
| 5,012,822 A | 5/1991 | Schwarz |
| 5,035,696 A | 7/1991 | Rydell |
| 5,057,106 A | 10/1991 | Kasevich et al. |
| 5,098,429 A | 3/1992 | Sterzer |
| 5,140,999 A | 8/1992 | Ardito |
| 5,190,517 A | 3/1993 | Zieve et al. |
| 5,281,217 A | 1/1994 | Edwards et al. |
| 5,309,910 A | 5/1994 | Edwards et al. |
| 5,314,465 A | 5/1994 | Maurer |
| 5,314,466 A | 5/1994 | Stern et al. |
| 5,330,518 A | 7/1994 | Neilson et al. |
| 5,348,554 A | 9/1994 | Imran et al. |
| 5,370,671 A | 12/1994 | Maurer et al. |
| 5,370,675 A | 12/1994 | Edwards et al. |
| 5,385,544 A | 1/1995 | Edwards et al. |
| 5,405,346 A | 4/1995 | Grundy et al. |
| 5,417,208 A | 5/1995 | Winkler |
| 5,423,811 A | 6/1995 | Imran |
| 5,437,662 A | 8/1995 | Nardella |
| 5,437,664 A | 8/1995 | Cohen et al. |
| 5,458,596 A | 10/1995 | Lax et al. |
| 5,480,417 A | 1/1996 | Hascoet et al. |
| 5,496,312 A | 3/1996 | Klicek |
| 5,514,130 A | 5/1996 | Baker |
| 5,540,679 A | 7/1996 | Fram et al. |
| 5,545,137 A | 8/1996 | Rudie et al. |
| 5,556,396 A | 9/1996 | Cohen et al. |
| 5,588,960 A | 12/1996 | Edwards et al. |
| 5,628,770 A | 5/1997 | Thome |
| 5,647,871 A | 7/1997 | Levine et al. |
| 5,649,973 A | 7/1997 | Tierney et al. |
| 5,674,220 A | 10/1997 | Fox et al. |
| 5,697,281 A * | 12/1997 | Eggers et al. ............... 604/114 |
| 5,700,261 A | 12/1997 | Brinkerhoff |
| 5,735,280 A | 4/1998 | Sherman et al. |
| 5,746,224 A | 5/1998 | Edwards |
| 5,755,753 A | 5/1998 | Knowlton |
| 5,769,879 A | 6/1998 | Richards et al. |
| 5,792,140 A | 8/1998 | Tu et al. |
| 5,807,395 A | 9/1998 | Mulier et al. |
| 5,810,808 A * | 9/1998 | Eggers ........................ 606/48 |
| 5,810,847 A | 9/1998 | Laufer et al. |
| 5,871,524 A | 2/1999 | Knowlton |
| 5,895,417 A | 4/1999 | Pomeranz et al. |
| 5,919,219 A | 7/1999 | Knowlton |
| 5,948,011 A | 9/1999 | Knowlton |
| 5,957,920 A | 9/1999 | Baker |
| 5,972,416 A | 10/1999 | Reimels et al. |
| 6,014,589 A | 1/2000 | Farley et al. |
| 6,015,407 A | 1/2000 | Rieb et al. |
| 6,016,452 A | 1/2000 | Kasevich |
| 6,022,346 A | 2/2000 | Panescu et al. |
| 6,032,078 A | 2/2000 | Rudie |
| 6,032,674 A * | 3/2000 | Eggers et al. ............... 128/898 |
| 6,035,238 A * | 3/2000 | Ingle et al. ................... 607/98 |
| 6,044,846 A | 4/2000 | Edwards |
| 6,044,847 A | 4/2000 | Carter et al. |
| 6,053,909 A * | 4/2000 | Shadduck ..................... 606/3 |
| 6,081,749 A | 6/2000 | Ingle et al. |
| 6,091,995 A | 7/2000 | Carter et al. |
| 6,139,569 A | 10/2000 | Ingle et al. |
| 6,156,060 A | 12/2000 | Ingle et al. |
| 6,179,769 B1 | 1/2001 | Ishikawa et al. |
| 6,216,704 B1 * | 4/2001 | Ingle et al. ................. 128/898 |
| 6,224,593 B1 | 5/2001 | Ryan et al. |
| 6,236,891 B1 | 5/2001 | Ingle et al. |
| 6,283,987 B1 * | 9/2001 | Laird et al. .................. 607/96 |
| 6,292,700 B1 | 9/2001 | Carter et al. |
| 6,322,584 B1 | 11/2001 | Ingle et al. |
| 6,350,276 B1 | 2/2002 | Knowlton |
| 6,364,879 B1 * | 4/2002 | Chen et al. ................... 606/45 |
| 6,416,504 B1 | 7/2002 | Ingle et al. |
| 6,453,202 B1 | 9/2002 | Knowlton |
| 6,461,332 B1 | 10/2002 | Ingle et al. |
| 6,533,780 B1 * | 3/2003 | Laird et al. ................... 606/41 |
| 6,558,381 B1 | 5/2003 | Ingle et al. |
| 6,579,266 B1 | 6/2003 | Ingle et al. |
| 6,629,535 B1 | 10/2003 | Ingle et al. |

FOREIGN PATENT DOCUMENTS

| | | |
|---|---|---|
| WO | WO 96/00041 | 1/1996 |
| WO | WO 96/00042 | 1/1996 |
| WO | WO 96/34568 | 11/1996 |
| WO | WO 97/15238 | 5/1997 |
| WO | WO 97/20510 | 6/1997 |
| WO | WO 97/24992 | 7/1997 |
| WO | WO 97/32532 | 9/1997 |
| WO | WO 97/39688 | 10/1997 |
| WO | WO 97/43970 | 11/1997 |
| WO | WO 97/43971 | 11/1997 |
| WO | WO 98/05286 | 2/1998 |
| WO | WO 98/05380 | 2/1998 |
| WO | WO 98/07468 | 2/1998 |
| WO | WO 98/38936 | 9/1998 |
| WO | WO 99/16502 | 4/1999 |
| WO | WO 00/06246 | 2/2000 |

* cited by examiner

RIBBED ELECTRODES AND METHODS FOR THEIR USE

CROSS-REFERENCES TO RELATED APPLICATION

This application claims the benefit of priority from U.S. patent application Ser. No. 09/925,501 filed on Oct. 23, 2000; now U.S. Pat. No. 6,533,780, which is a continuation of U.S. patent application Ser. No. 09/229,508 filed on Jan. 12, 1999 now U.S. Pat. No. 6,283,987, and further claims the benefit of priority from U.S. Provisional Patent Application Ser. No. 60/071,324 filed on Jan. 14, 1998, the full disclosures of which are incorporated herein by reference.

BACKGROUND OF THE INVENTION

1. Field of the Invention

The present invention generally relates to medical devices, methods, and systems. More specifically, the present invention provides techniques for selectively heating and shrinking tissues, particularly for the noninvasive treatment of urinary incontinence and hernias, for cosmetic surgery, and the like.

Urinary incontinence arises in both women and men with varying degrees of severity, and from different causes. In men, the condition occurs almost exclusively as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external sphincter, and most often, to the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such noninterventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

Each of these procedures has associated shortcomings. Surgical operations which involve suturing of the tissue structures supporting the urethra or bladder neck region require great skill and care to achieve the proper level of artificial support. In other words, it is necessary to occlude or support the tissues sufficiently to inhibit urinary leakage, but not so much that intentional voiding is made difficult or impossible. Balloons and other bulking agents which have been inserted can migrate or be absorbed by the body. The presence of such inserts can also be a source of urinary tract infections. Therefore, it would be desirable to provide an improved therapy for urinary incontinence.

A variety of other problems can arise when the support tissues of the body have excessive length. Excessive length of the pelvic support tissues (particularly the ligaments and fascia of the pelvic area) can lead to a variety of ailments including, for example, cystocele, in which a portion of the bladder protrudes into the vagina. Excessive length of the tissues supporting the breast may cause the breasts to sag. Many hernias are the result of a strained, torn, and/or distended containing tissue, which allows some other tissue or organ to protrude beyond its contained position. Cosmetic surgeries are also often performed to decrease the length of support tissues. For example, abdominoplasty (often called a "tummy tuck") is often performed to decrease the circumference of the abdominal wall. The distortion of these support tissues may be due to strain, advanced age, congenital predisposition, or the like.

Unfortunately, many support tissues are difficult to access, and their tough, fibrous nature can complicate their repair. As a result, the therapies now used to improve or enhance the support provided by the ligaments and fascia of the body often involve quite invasive surgical procedures.

For these reasons, it would be desirable to provide improved devices, methods, and systems for treating fascia, tendons, and the other support tissues of the body. It would be particularly desirable to provide improved noninvasive or minimally invasive therapies for these support tissues, especially for the treatment of urinary incontinence in men and women. It would further be desirable to provide treatment methods which made use of the existing support structures of the body, rather than depending on the specific length of an artificial support structure.

2. Description of the Background Art

U.S. Pat. No. 5,423,811 describes a method for RF ablation using a cooled electrode. U.S. Pat. Nos. 5,458,596 and 5,569,242 describe methods and an apparatus for controlled contraction of soft tissue. An RF apparatus for controlled depth ablation of soft tissue is described in U.S. Pat. No. 5,514,130.

U.S. Pat. No. 4,679,561 describes an implantable apparatus for localized heating of tissue, while U.S. Pat. No. 4,765,331 describes an electrosurgical device with a treatment arc of less than 360 degrees. An impedance and temperature generator control is described in U.S. Pat. No. 5,496,312. Bipolar surgical devices are described in U.S. Pat. Nos. 5,282,799, 5,201,732, and 728,883.

SUMMARY OF THE INVENTION

In a first aspect, the present invention provides a probe comprising a first electrode having a first electrode surface with a first edge. A second electrode has a second electrode surface with a second edge adjacent the first edge. The first and second surfaces are aligned so as to simultaneously engage a tissue surface. An insulator is disposed between the first and second electrode. The insulator extends beyond the edges so as to avoid edge induced concentration of current flux. The insulator will typically comprise a protruding rib or a film.

In a second aspect, the present invention provides a probe comprising a first electrode having a first electrode surface for engaging a tissue surface of a tissue. A second electrode has a second electrode surface which is oriented to engage the tissue surface simultaneously with the first electrode surface. A rib between the first and second electrodes extends beyond the electrode surfaces so as to protrude into the tissue.

The rib will generally be electrically isolated from the first and second electrodes, so that the rib can direct a bi-polar current flux between the electrode surfaces into the tissue beyond the protruding rib. The rib may be adapted to distend the tissue surface (for example, by providing a rounded protruded edge, or by forming the rib from a soft material), or may instead be adapted to incise the tissue surface (for example, by forming the rib with a sharp and/or hard protruding edge). Preferably, a cooling system will be coupled to the first and second electrodes for cooling the engaged tissue surface.

The ribbed probe of the present invention is particularly well adapted for directing current flux through an intermediate tissue and into a collagenous target tissue so as to heat and shrink the collagenous tissue. Cooling of the electrode surfaces can help minimize collateral damage to the intermediate tissue during this process.

In another aspect, the invention provides a probe comprising first and second electrically and thermally conductive tubes. Each of the tubes has an electrode surface and a side surface with an edge therebetween. An electrical insulation film is disposed between the side surfaces of the tubes. The film is thermally conductive and has an exposed cooling surface extending between the electrode surfaces of the tubes, and cooling surface being thermally coupled to a cooling fluid.

Advantageously, the film can avoid electrical current concentrations (and localized overheating) at the edges of the electrode surfaces, while applying cooling contiguously across a pair of separated bipolar electrodes.

DESCRIPTION OF THE SPECIFIC EMBODIMENTS

Figure 1:
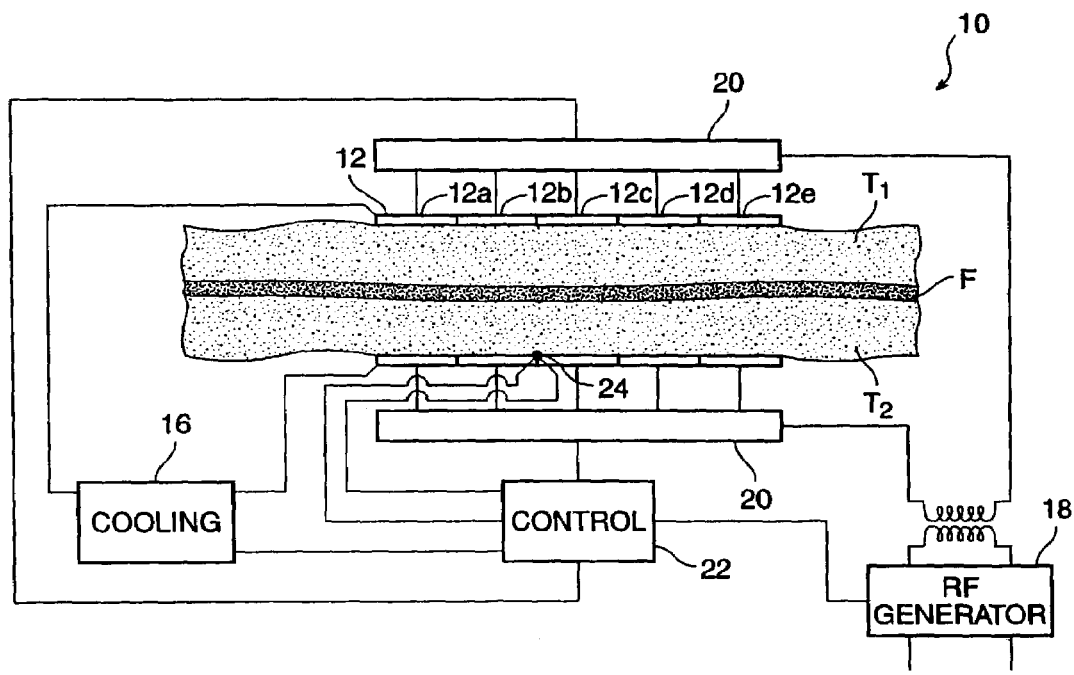
FIG. 1 is a schematic illustration of a system for heating and shrinking fascia disposed between adjacent tissue layers by heating the fascia between a pair of large, cooled, flat electrode arrays, according to the principles of the present invention.

The present invention optionally relies on inducing controlled shrinkage or contraction of a support tissue of the body, typically being a collagenous tissue such as fascia, ligament, or the like. For treatment of urinary incontinence, the tissue structure will be one that is responsible in some manner for control of urination, or for supporting a such a tissue. Exemplary tissue structures include the urethral wall, the bladder neck, the bladder, the urethra, bladder suspension ligaments, the sphincter, pelvic ligaments, pelvic floor muscles, fascia, and the like. Treatment of other conditions may be effected by selective shrinking of a wide variety of other tissues, including (but not limited to) the diaphragm, the abdominal wall, the breast supporting ligaments, the fascia and ligaments of the joints, the collagenous tissues of the skin, and the like. Related devices, methods, and system are also described in co-pending U.S. patent application Ser. No. 08/910,370, filed Aug. 13, 1997, the full disclosure of which is incorporated herein by reference.

Tissue contraction results from controlled heating of the tissue by affecting the collagen molecules of the tissue. Contraction occurs as a result of heat-induced uncoiling and repositioning of the collagen β-pleated structure. By maintaining the times and temperatures set forth below, significant tissue contraction can be achieved without substantial collateral tissue necrosis.

The temperature of the target tissue structure will generally be raised to a value in the range from about 60° C. to 110° C., often being in the range from about 60° C. to 80° C., and will generally effect a shrinkage of the target tissue in at least one dimension of between about 20 and 50 percent. In many embodiments, heating energy will be applied for a period of from 30 seconds to 5 minutes. These heating times will vary with separation between the parallel plate electrodes, with a heat time of about 5 minutes often being appropriate for an electrode separation of about 4 cm. Shorter heat times may be used with smaller electrode separation distances.

The rise in temperature may be quite fast, although there will often be advantages in heating tissues more slowly, as this will allow more heat to be removed from tissues which are not targeted for therapy, thereby minimizing collateral damage. However, if too little heating energy is absorbed by the tissue, blood perfusion will transfer the heat away from the targeted tissue, so that the temperature will not rise sufficiently to effect therapy. Fortunately, fascia and other support tissues often have less blood flow than adjacent tissues and organs; this may help enhance the heating of fascia and minimize necrosis of the surrounding structures.

The total amount of energy delivered will depend in part on which tissue structure is being treated, how much tissue is disposed between the target tissue and the heating element, and the specific temperature and time selected for the protocol. The power delivered will often be in the range from 10 W to 100 W, usually being about 20 W. The temperature will usually not drop instantaneously when the heating energy stops, so that the tissue may remain at or near the therapy temperature for a time from about 10 seconds to about 2 minutes, and will often cool gradually back to body temperature.

While the remaining description is generally directed at devices and methods for treatment of urinary stress incontinence of a female patient, it will be appreciated that the present invention will find many other applications for selectively directing therapeutic heating energy into the tissues of a patient body for shrinking of tissues, for ablation of tissues and tumors, and the like.

FIG. 1 schematically illustrates a system 10 for shrinking a fascia F disposed between first and second adjacent tissues T1, T2. System 10 includes a pair of electrodes 12, 14 having large, substantially planar tissue engaging surfaces. Electrodes 12, 14 are aligned substantially parallel to each other with the fascia (and adjacent tissues) disposed therebetween.

The surfaces of electrodes 12, 14 which engage the tissue are cooled by a cooling system 16. The cooling system will typically include a conduit through the electrode for the circulation of a cooling fluid, but may optionally rely on thermoelectric cooling or the like. The temperature of the electrode surface may be regulated by varying the temperature or flow rate of the cooling fluid. Cooling may be provided through the use of an ice bath, by endothermic chemical reactions, by standard surgical room refrigeration mechanisms, or the like. Ideally, the cooling system cools an area which extends beyond the energized electrode surfaces to prevent any hot spots adjacent the tissue surface, and to maximize the heat removal from the tissue without having to resort to freezing the tissue.

Each of the electrodes is separated into a plurality of electrode segments. For example, the electrode includes electrode segments 12a, 12b, 12c, 12d, and 12e, each of which is electrically isolated from the others. This allows the electrode segments to be individually energized.

Electrodes 12, 14 are energized by a radiofrequency (RF) power source 18. Multiplexers 20 individually energize each electrode segment, typically varying the power or time each segment is energized to more nearly uniformly heat fascia F. A controller 22 will typically include a computer program which directs the application of cooling flow and RF power through electrodes 12, 14, ideally based at least in part on a temperature signal sensed by a temperature sensor 24. Temperature sensor 24 may sense the temperature of the tissue at the tissue/electrode interface, or may alternatively sense the temperature of the fascia itself.

Figure 2:
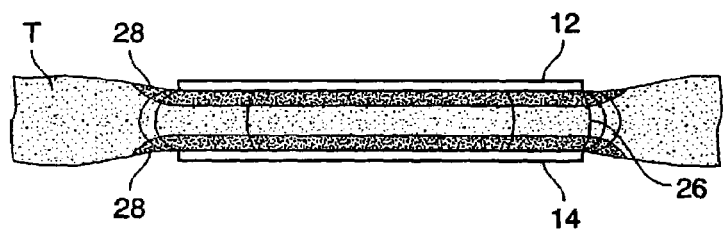
FIG. 2 schematically illustrates the even heating provided by a current flux between the large, cooled, flat electrode surfaces of the system of FIG. 1.

The use of large cooled plate electrodes to direct an even electrical current flux can be understood with reference to the simplified cross-sectional illustration of FIG. 2. In this example, RF power is applied uniformly across parallel plate electrodes 12, 14 to produce a current through tissue T. As the electrode surfaces are substantially planar, and as the electrode surfaces are large compared to the separation between the electrodes, a current flux 26 is substantially uniform throughout that portion of the tissue which is disposed between the electrode surfaces. The flow of electrical current through the electrical resistance of the tissue causes the temperature of the tissue through which the current passes to rise. The use of relatively low radiofrequency current, preferably in the range from 100 kHz to 1 MHz, helps to avoid collateral damage to nerve and muscle tissues.

Preliminary work in connection with the present invention has shown that fascia and other collagenated tissues which are heated to a temperature range of between about 60° C. and 110° C., and preferably between about 60° C. and 80° C., will contract. In fact, unstressed fascia will shrink between about 30% and 50% when heated for a very short time, preferably from between about 0.5 seconds to 5 seconds. Such heating can easily be provided by conduction of RF currents through the tissue.

The uniform current flux provided by the large plate electrodes of the present invention will produce a substantially uniform heating of the tissue which passes that current. To selectively target a central portion of the tissue, in other words, to selectively heat a target portion of the tissue separated from electrodes 12, 14, the electrode surfaces are cooled. This cooling maintains a cooled tissue region 28 adjacent each electrode below a maximum safe tissue temperature, typically being below about 45° C. Even though heat generation throughout the gap between the electrodes is uniform, the temperature profile of the tissue between the electrodes can be controlled by removing heat through the electrode surfaces during heating.

Generally, sufficient heating can be provided by a current of between about 0.2 and 2.0 amps, ideally about 1.0 amp, and a maximum voltage of between about 30 and 100 volts rms, ideally being about 60 volts rms. The electrodes will often have a surface area of between about 5.0 and 200 cm2, and the current density in the target tissue will often be between about 1 mA/cm2 and 10 mA/cm2. This will provide a maximum power in the range from about 10W to about 100W, often being about 20 watts. Using such low power settings, if either electrode is lifted away from the engaged tissue, there will be no arcing. Instead, the current will simply stop. This highlights the difference between the electrical tissue heating of the present invention and known electrocautery techniques.

The ideal geometry to provide a true one-dimensional temperature distribution would include large parallel plate electrodes having relatively minimal spacing therebetween. As tissues which are easily accessible for such structures are fairly limited, the present invention can also make use of electrode geometries which vary somewhat from this ideal, particularly through the use of array electrodes. In fact, the use of a single array electrode, in combination with a much larger, uncooled electrode pad may heat tissues disposed near the array, as will be described hereinbelow. Nonetheless, uniform heating is generally enhanced by providing electrode structures having tissue engaging surfaces which are as flat and/or as parallel as practical. Preferably, the parallel electrode surfaces will be separated by between about ⅓ and 1.0 times the width of the electrode surfaces (or of the smaller surface, if they are different).

Figure 2A:
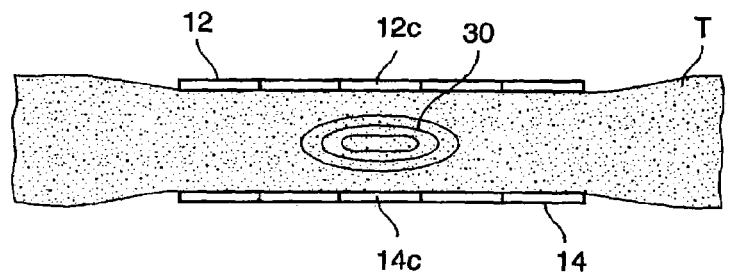
FIGS. 2A–2F schematically illustrate structures and methods for selectively energizing the electrode surface segments of the large, flat electrode arrays of the system of FIG. 1 to tailor the current flux throughout a target zone.
Figure 2B:
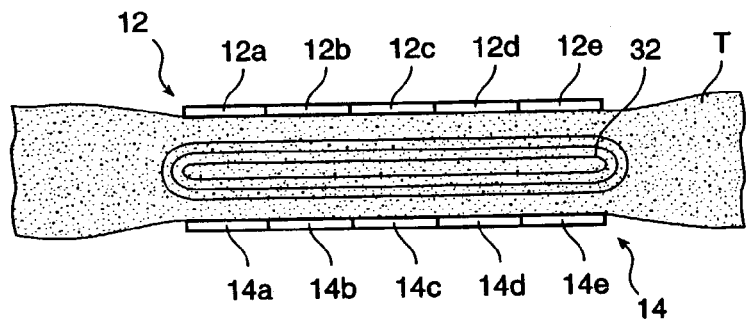

The use of an array electrode having multiple electrode segments can be understood with reference to FIGS. 2A–2D. FIG. 2A schematically illustrates the shape of a target zone which is heated by selectively energizing only electrode segments 12c and 14c of cooled electrodes 12 and 14. Once again, it should be understood that the temperature of target zone 32 (here illustrated schematically with isotemperature contour lines 30) is the result of uniform heating between the energized electrode segments, in combination with cooling of tissue T by the electrode surfaces. To expand the heated area laterally between the electrodes, electrode segments 12a, 12b, 12c . . . , and 14a, 14b, 14c . . . , can be energized, thereby heating an entire target zone 32 extending throughout tissue T between the electrodes.

Figure 2C:
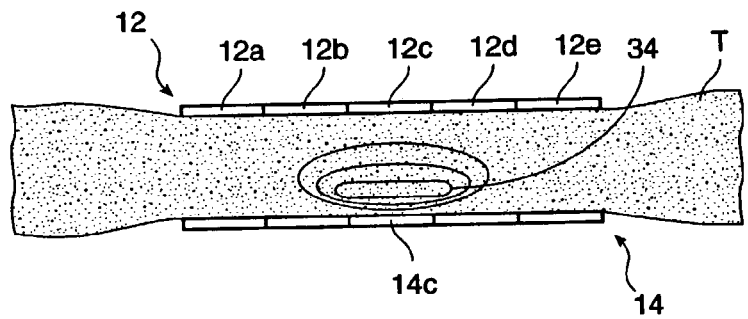

The use of array electrodes provides still further flexibility regarding the selective targeting of tissues between electrodes 12 and 14. As illustrated in FIG. 2C, selectively energizing a relatively large effective electrode surface by driving electrodes segments 12a, 12b, 12c, 12d, and 12e results in a low current flux which is widely disbursed throughout the tissue T engaged by electrode 12. By driving this same current through a relatively small effective electrode surface using only a single electrode surface segment 14c produces an offset target zone 34 which is much closer to electrode 14 than to electrode 12.

Figure 2D:
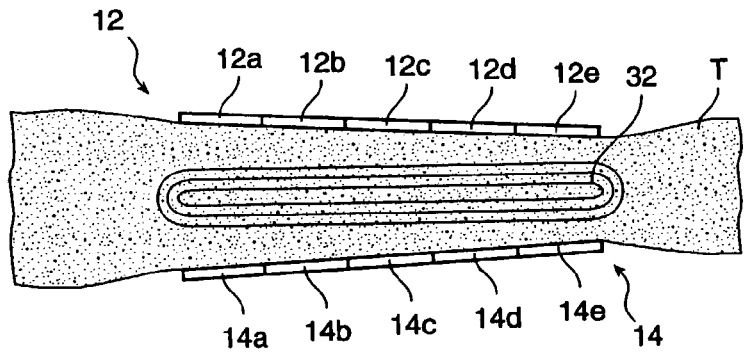

To compensate for electrode structures which are not exactly parallel, varying amounts of electrical current can be provided to the electrode segments. For example, a fairly uniform target zone 32 may be heated between angled electrodes by driving more current through relatively widely spaced electrode segments 12a, 14a, and driving less current through more tightly spaced electrode segments 12e, 14e, as illustrated in FIG. 2D. It should be understood that these selective targeting mechanisms may be combined to target fascia and other tissues which are near one slanted electrode, or to selectively target only a portion of the tissues disposed between relatively large electrode arrays.

Figure 2E:
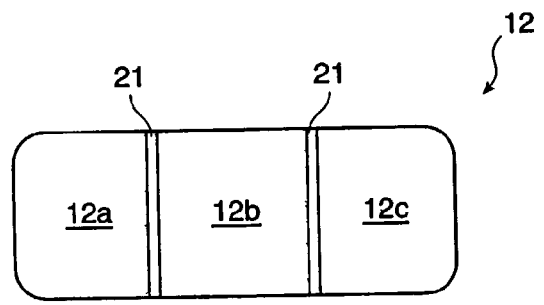
Figure 2F:
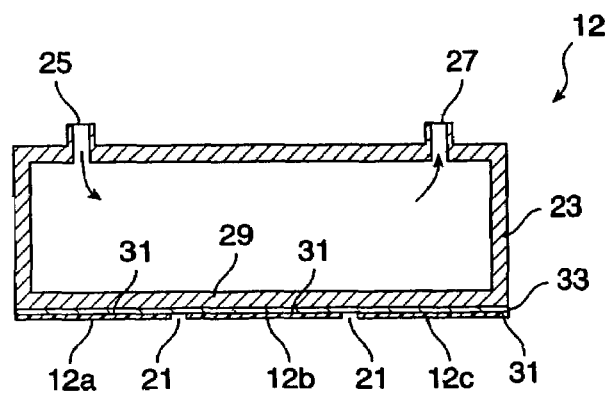

An exemplary structure for segmented, cooled electrode 12 is schematically illustrated in FIGS. 2E and F. Electrode 12 here comprises three electrode surface segments 12a, 12b, and 12c separated by insulating spaces 21. A plastic housing 23 defines a flow path between a cooling inflow port 25 and a cooling outflow port 27, while heat transfer between the cooling fluid and the electrode surface is enhanced by a thermally conductive front plate 29. Front plate 29 generally comprises a thermally conductive metal such as aluminum. Electrode surface segments 12a, 12b, and 12c may comprise surfaces of separated segments 31 of aluminum foil. Segments 31 may be electrically isolated by a mylar insulation sheet 33 disposed between the segments and front plate 29.

The array electrode structures of the present invention will generally include a series of conductive surface segments which are aligned to define a substantially flat electrode surface. The electrode surface segments are separated by an electrically insulating material, with the insulation being much smaller in surface area than the conductive segments. Typically, there will be between 1 and 8 electrode segments, which are separated by a distance of between about 0.25 mm and 1.0 mm.

In some embodiments, the peripheral edges of the electrode segments may be rounded and/or covered by an insulating material to prevent concentrations of the electrical potential and injury to the engaged tissue surfaces.

It should also be understood that while the electrode arrays of the present invention are generally herein described with reference to a linear array geometry, the present invention also encompasses electrodes which are segmented into two-dimensional arrays. Where opposed sides of the tissue are accessible for relatively large array structures, such as along the exposed skin, or near the major cavities and orifices of the body, the electrode surfaces will preferably be separated by a gap which is less than a width (and length) of the electrodes.

In some embodiments, one electrode structure may be disposed within a large body cavity such as the rectum or vagina, while the other is placed in an adjacent cavity, or on the skin so that the region to be treated is between the electrode surfaces. In other embodiments, one or both electrodes may be inserted and positioned laparoscopically. It will often be desirable to clamp the tissue tightly between the electrodes to minimize the gap therebetween, and to promote efficient coupling of the electrode to the tissue.

Figure 2G:
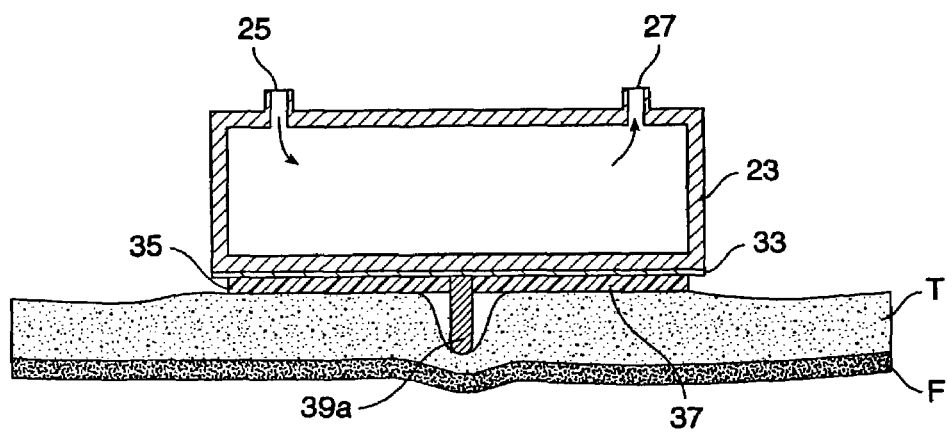
FIGS. 2G and H illustrate a probe structure in which an insulator is disposed between the electrodes to prevent edge induced current flux concentration, thereby enhancing the probe's ability to direct a current flux deep into tissues without inducing collateral damage at the engaged tissue surface.

Referring now to FIGS. 2G and H, an alternative cooled electrode structure for use with any of the methods, devices, and systems described herein makes use of an insulator between electrodes and/or electrode segments to minimize edge induced current concentration. By positioning an insulating rib or film between electrodes, the RF current can be directed over the insulator without having to resort to widely spaced electrodes or electrode segments, large radiused edges, and the like.

In general, when two planar electrodes are disposed side-by-side on a flat (or large radius) surface for the application of RF energy, maximum heating will occur at the edges of the electrodes. This non-uniform heating is caused by the concentration of electrical potential at these locations. For this reason, it is often preferable to round the edges of plate electrodes. To further reduce the current density between electrodes, the edges of bi-polar electrodes (or differentially powered electrode segments) will also often be separated by a greater distance than might otherwise be desirable for applying uniform therapeutic heating, such as to shrink collagenated tissue.

To avoid the concentration of heating at the adjacent edges of electrodes 35 and 37, an insulating rib 39a is positioned roughly perpendicular to, and disposed between, the two plate electrodes. Electrical current very near the surface of an insulator will generally flow parallel to the insulator surface. In contrast, current which is very near a conductor will generally flow perpendicular to the conductor surface. In the absence of rib 39a, the current density is greatest directly between the two electrodes at their adjacent edges, and will tend to cause a burn at that location.

By providing vertical rib 39a between the electrode surfaces, the current can be directed away from the electrodes and over the protruding rib. As a result, the rib will tend to induce a region of approximately parallel current flow beyond the end of the protruding rib and roughly perpendicular to the electrode surfaces. Advantageously, rib 39a directs the greatest current density deep into the tissue, allowing a bi-polar current between the electrodes to heat and shrink fascia F without inducing a burn at the surface of intermediate tissue T. In some embodiments, rib 39a may distend the engaged tissue surface. Alternatively, a sharpened rib may incise the tissue to direct the heating current flux deeper through the intermediate tissue and into an inaccessible target tissue.

Figure 2H:
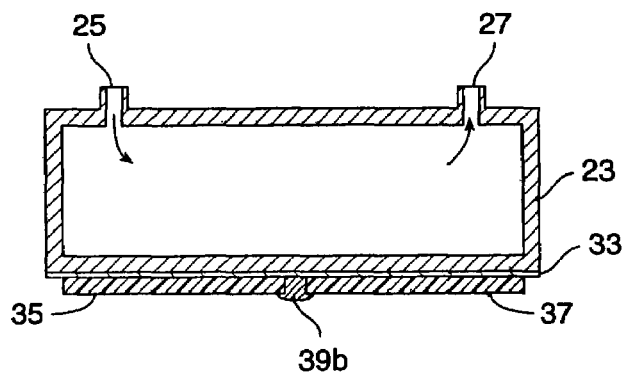

In alternative embodiments, the insulator may comprise a film 39b as illustrated in FIG. 2H. Film 39b is disposed between electrodes 35, 37, and extends over the adjacent edges of the electrodes to avoid edge induced concentration of current flux at this location.

Figure 3:
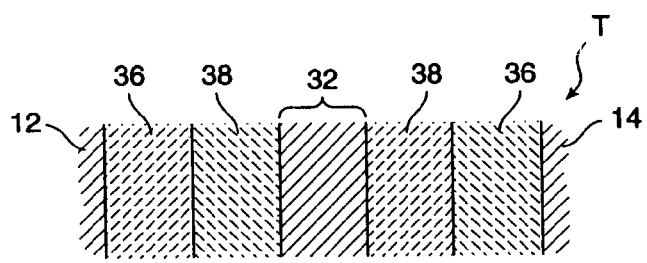
FIGS. 3–3E graphically illustrate a method for heating a target tissue between cooled electrodes, wherein the electrode surfaces cool the tissue before, during, and after radiofrequency energy is applied.
Figure 3A:
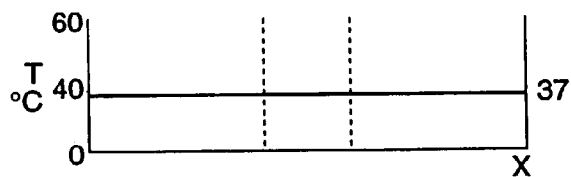
Figure 3B:
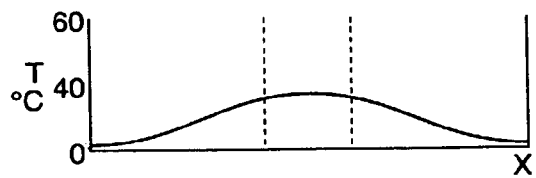
Figure 3C:
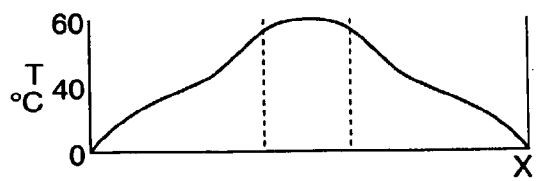
Figure 3D:
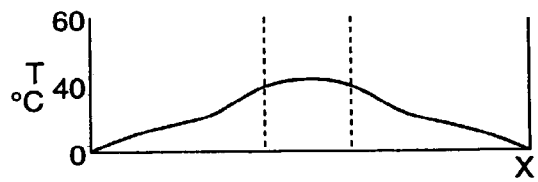
Figure 3E:
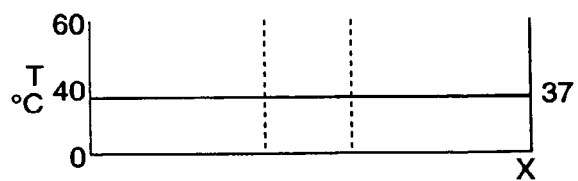

As can be understood with reference to FIGS. 3–3E, the tissue will preferably be cooled before and after energizing of the electrodes. FIG. 3 illustrates three distinct regions of tissue T disposed between electrodes 12 and 14. Target zone 32 will typically comprise fascia or some other collagenated tissue, while the surfaces of the electrodes engage an intermediate tissue 36 disposed on either side of the fascia.

It will generally be desirable to maintain the temperature of intermediate tissue 36 below a maximum safe tissue temperature to prevent injury to this intermediate tissue, the maximum safe tissue temperature typically being about 45° C. To effect shrinkage of fascia, target zone 32 will typically be heated to a temperature above about 60° C.

There will often be a region of stunned tissue 38 disposed between the safely cooled intermediate tissue 36 and the target zone 32. This stunned tissue will typically be heated in the range from about 45° C. to about 60° C., and may therefore undergo some limited injury during the treatment process. As a result, it is generally desirable to minimize the time this tissue is at an elevated temperature, as well as the amount of stunned tissue.

As illustrated in FIG. 3A, prior to application of cooling or heating energy, the temperature profile of tissue T along an axis X between electrodes 12 and 14 is substantially uniform at body temperature. The tissue will preferably be pre-cooled by the surfaces of electrodes 12, 14, generally using an electrode surface temperature of at or above 0° C. Pre-cooling will substantially decrease the temperature of intermediate tissues 36, and will preferably at least partially decrease the temperature of stunned tissue 38. At least a portion of the target zone remains at or near the initial body temperature, as illustrated in FIG. 3B. Pre-cooling time will often depend on electrode separation and tissue heat diffusity.

Once the tissue has been pre-cooled, the RF current is directed through the tissue between the electrodes to heat the tissue. A temperature sensor can be placed at the center of target zone 32 to help determine when the pre-cooling has been applied for the proper time to initiate RF heating. The current flux applies a fairly uniform heating throughout the tissue between the electrodes, and the electrode surfaces are often cooled throughout the heating process. As target zone 32 has the highest temperature upon initiation of the heating cycle, and as the target zone is farthest from the cooled electrodes, a relatively small amount of heat flows from the target zone into the electrodes, and the target zone is heated to a significantly higher temperature than intermediate tissue 36.

Heat is applied until the target zone is at or above a treatment temperature, typically resulting in a temperature distribution such as that illustrated in FIG. 3C. To minimize collateral damage to the adjacent tissues 36 and stunned tissue 38, the cooling system continues to circulate cold fluid through the electrode, and to remove heat from the tissue, after the heating radiofrequency energy is halted. When substantially the entire tissue is below the maximum safe tissue temperature (as in FIG. 3D), cooling can be halted, and the tissue can be allowed to return to standard body temperature, as illustrated in FIG. 3E.

Optionally, RF current may be driven between the two cooled plate electrodes using intermittent pulses of excitation. As used herein, intermittent or pulsed excitation encompasses cyclically increasing and decreasing delivered power, including cyclical variations in RMS power provided by amplitude modulation, waveform shape modulation, pulse width modulation, or the like. Such intermittent excitation will preferably provide no more than about 25% of the RMS power of the pulses during the intervals between pulses. Preferably, the electrodes will be energized for between about 10 and 50% of a total heating session. For example, electrodes 12 and 14 may be energized for 15 secs. and then turned off for 15 secs. and then cycled on and off again repeatedly until the target tissue has been heated sufficiently to effect the desired shrinkage. Preferably, the electrode surfaces (and the surrounding probe structure which engages the tissue) will be cooled throughout the on/off cycles of the heating sessions.

The therapeutic heating and cooling provided by the electrodes of the present invention will often be verified and/or controlled by sensing the temperature of the target tissue and the adjacent tissue directly. Such temperature sensing may be provided using a needle containing two temperature sensors: one at the tip to be positioned at the center of the treatment zone, and the second along the shaft of the needle so as to be positioned at the edge of the desired protection zone. In other words, the second sensor will be placed along the border between the intermediate tissue and the target tissue, typically somewhere along stunned tissue 38. The temperature sensors will preferably sense the tissue temperature during the intervals between pulses to minimize errors induced by the heating RF current flux in the surrounding tissue. The temperature sensors may comprise thermistors, thermocouples, or the like.

The temperature sensing needle may be affixed to or advanceable from a probe supporting the electrode adjacent to or between the electrode segments. Alternatively, two or more needles may be used. Typically, controller 22 will provide signals to cooling system 16 and the electrodes so that the electrodes chill the engaged tissue continually while the RF current is pulsed to increase the temperature of the treatment zone incrementally, ideally in a step-wise manner, until it reaches a temperature of 60° C. or more, while at the same time limiting heating of the intermediate tissue to 45° C. or less per the feedback from the needles.

In alternative embodiments, pre-chilling time, the duration of the heat, the lengths of the heating intervals (and the time between heating intervals) during intermittent heating, and the radiofrequency heating current may be controlled without having direct feedback by using dosimetry. Where the thermal properties of these tissues are sufficiently predictable, the effect of treatment can be estimated from previous measurements.

Figure 4:
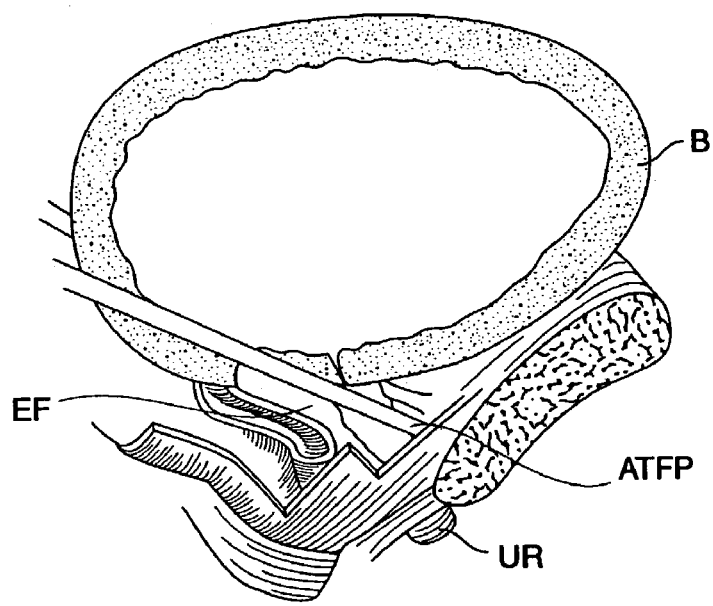
FIG. 4 is a cut-away view illustrating pelvic support structures which can be targeted for non-invasive selective contraction using the methods of the present invention.

The pelvic support tissues which generally maintain the position of the urinary bladder B are illustrated in FIG. 4. Of particular importance for the method of the present invention, endopelvic fascia EF defines a hammock-like structure which extends between the arcus tendineus fascia pelvis ATFP. These latter structures extend between the anterior and posterior portions of the pelvic bone, so that the endopelvic fascia EF largely defines the pelvic floor.

In women with urinary stress incontinence due to bladder neck hypermobility, the bladder has typically dropped between about 1.0 cm and 1.5 cm (or more) below its nominal position. This condition is typically due to weakening of the pelvic support structures, including the endopelvic fascia, the arcus tendineus fascia pelvis, and the surrounding ligaments and muscles, often as the result of bearing children.

When a woman with urinary stress incontinence sneezes, coughs, laughs, or exercises, the abdominal pressure often increases momentarily. Such pressure pulses force the bladder to descend still further, shortening the urethra UR and momentarily opening the urinary sphincter.

Figure 4A:
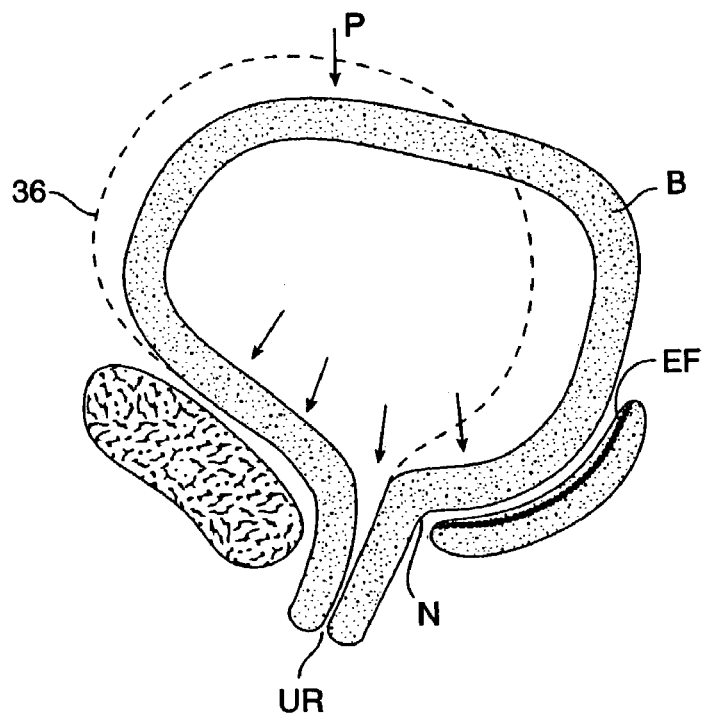
FIGS. 4A–4C illustrate contraction and reinforcing of the pelvic support tissues of FIG. 4 as a therapies for female urinary incontinence.
Figure 4B:
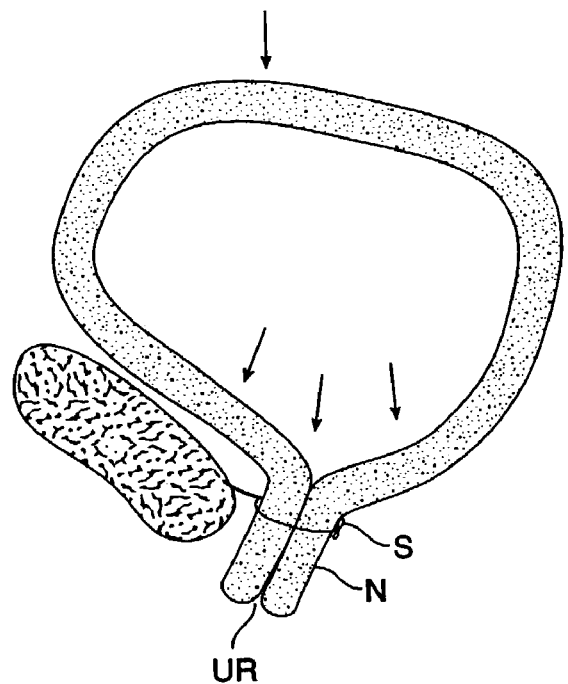
Figure 4C:
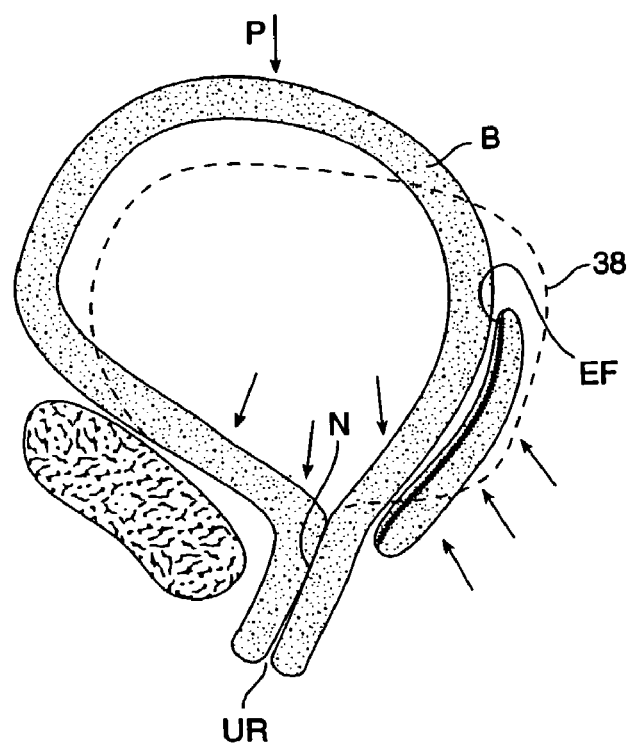

As can be most clearly understood with reference to FIGS. 4A–4C, the present invention generally provides a therapy which applies gentle heating to shrink the length of the support tissues and return bladder B to its nominal position. Advantageously, the bladder is still supported by the fascia, muscles, ligaments, and tendons of the body. Using gentle resistive heating between bipolar electrodes, the endopelvic fascia EF and arcus tendineus fascia pelvis ATFP are controllably contracted to shrink them and re-elevate the bladder toward its original position.

Referring now to FIG. 4A, bladder B can be seen to have dropped from its nominal position (shown in phantom by outline 36). While endopelvic fascia EF still supports bladder B to maintain continence when the patient is at rest, a momentary pressure pulse P opens the bladder neck N, resulting in a release through urethra UR.

A known treatment for urinary stress incontinence relies on sutures S to hold bladder neck N closed so as to prevent inadvertent voiding, as seen in FIG. 4B. Sutures S may be attached to bone anchors affixed to the pubic bone, ligaments higher in the pelvic region, or the like. In any case, loose sutures provide insufficient support of the bladder neck N and fail to overcome urinary stress incontinence, while overtightening of sutures S may make normal urination difficult and/or impossible.

As shown in FIG. 4C, by selectively contracting the natural pelvic support tissues, bladder B can be elevated from its lowered position (shown by lowered outline 38). A pressure pulse P is resisted in part by endopelvic fascia EF, which supports the lower portion of the bladder and helps maintain the bladder neck in a closed configuration. In fact, fine tuning of the support provided by the endopelvic fascia is possible through selective contraction of the anterior portion of the endopelvic fascia to close the bladder neck and raise bladder B upward. Alternatively, lateral repositioning of bladder B to a more forward position may be affected by selectively contracting the dorsal portion of endopelvic fascia EF. Hence, the therapy of the present invention may be tailored to the particular elongation exhibited by a patient's pelvic support tissues.

As is more fully explained in co-pending U.S. patent application Ser. No. 08/910,370, filed Aug. 13, 1997, previously incorporated by reference, a wide variety of alternative conditions may also be treated using the methods of the present invention. In particular, selective shrinkage of fascia may effectively treat cystocele, hiatal, and inguinal hernias, and may even be used in cosmetic procedures such as abdominoplasty (through selectively shrinking of the abdominal wall), to remove wrinkles by shrinking the collagenated skin tissues, or to lift sagging breasts by shrinking their support ligaments.

Figure 5:
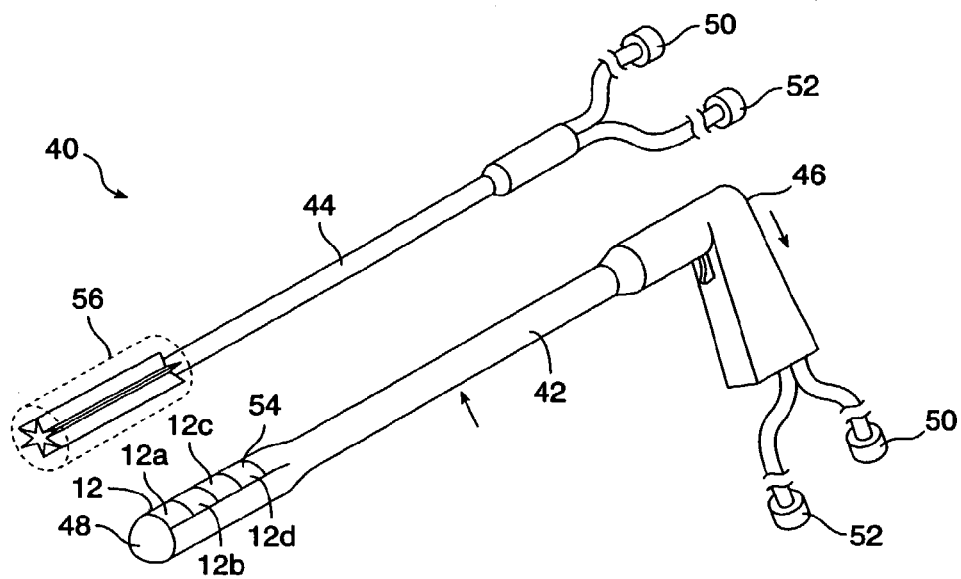
FIG. 5 is a perspective view of a system for treating female urinary incontinence by selectively shrinking the endopelvic fascia, according to the principles of the present invention.

A system for selectively shrinking the endopelvic fascia is illustrated in FIG. 5. System 40 includes a vaginal probe 42 and a bladder probe 44. Vaginal probe 42 has a proximal end 46 and a distal end 48. Electrode 12 (including segments 12a, 12b, 12c, and 12d) is mounted near the distal end of the probe. Vaginal probe 42 will typically have a diameter of between about 2 and 4 cm, and will often have a shaft length of between about 6 and 12 cm. An electrical coupling 50 is coupleable to an RF power supply, and optionally to an external control processor. Alternatively, a controller may be integrated into the probe itself. A fluid coupling 52 provides attachment to a cooling fluid system. Cooling fluid may be recycled through the probe, so that more than one fluid couplers may be provided.

The segments of electrode 12 are quite close to each other, and preferably define a substantially flat electrode surface 54. The cooling fluid flows immediately below this surface, the surface material preferably being both thermally and electrically conductive. Ideally, surface 54 is as large as the tissue region to be treated, and a thermocouple or other temperature sensor may be mounted adjacent the surface for engaging the tissue surface and measuring the temperature of the engaged tissue.

Figure 6:
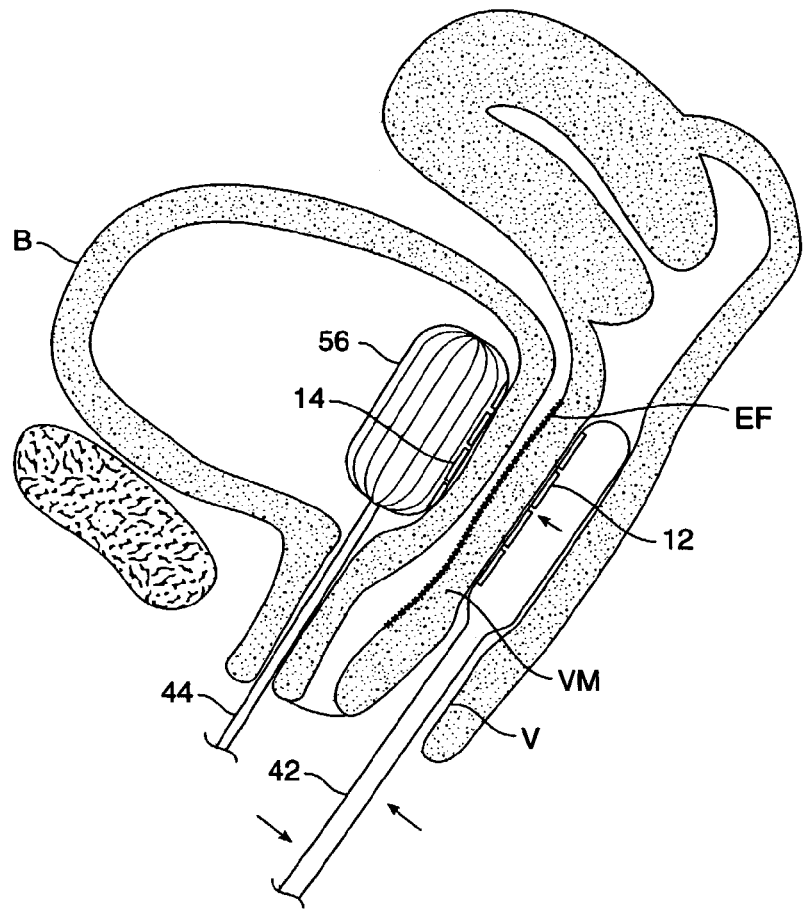
FIG. 6 is a cross-sectional view illustrating a method for using the system of FIG. 5 to treat female urinary incontinence.

Urethral probe 44 includes a balloon 56 supporting a deployable electrode surface. This allows the use of a larger electrode surface than could normally be inserted through the urethra, by expanding the balloon structure within the bladder as illustrated in FIG. 6. Alternatively, a narrower cylindrical electrode might be used which engages the surrounding urethra, the urethral electrode optionally being separated into more than one segment along the length and/or around the circumference of the probe shaft. Radiofrequency current will divert from such a tightly curved surface and heat the nearby tissue. The electrode can again be chilled to protect the urethral lining from thermal damage.

As illustrated in FIG. 6, the endopelvic fascia will preferably be disposed between the electrodes of the urethral probe 44 and vaginal probe 42 when the vaginal probe is levered to the right or left side of the pelvis by the physician. Balloon 56 of urethral probe 44 is here illustrated in its expanded configuration, thereby maximizing a surface area of electrode 14, and also minimizing its curvature (or, in other words, maximizing the radius of curvature of the electrode surface). Preferably, cooled fluid recirculating through balloon 56 will cool electrode 14, so that cooled electrodes 12, 14 will selectively heat the endopelvic fascia EF without damaging the delicate vaginal mucosa VM or the bladder wall.

Urethral probe 44 and vaginal probe 42 may optionally be coupleable to each other to facilitate aligning the probes on either side of the target tissue, either mechanically or by some remote sensing system. For example, one of the probes may include an ultrasound transducer, thereby facilitating alignment of the electrode surfaces and identification of the target tissue. Alternatively, the proximal ends of the probes may attach together to align the electrodes and/or clamp the target tissue between the probes.

Figure 7:
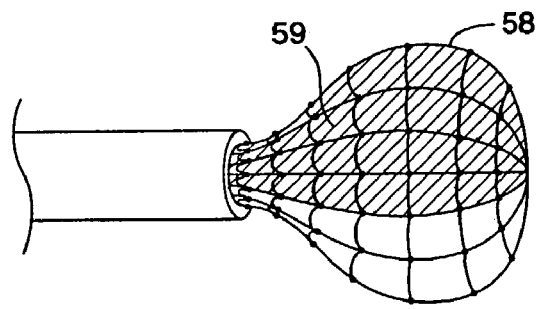
FIG. 7 illustrates an alternative bladder electrode structure for use in the method of FIG. 6.

Referring now to FIG. 7, a mesh electrode 58 may be unfurled within the bladder in place of urethral probe 44. Mesh electrode 58 preferably comprises a highly flexible conductive element, optionally being formed of a shape memory alloy such as Nitinol™. The bladder may be filled with an electrically non-conductive fluid such as distilled water during the therapy, so that little or no RF current would flow into the bladder wall beyond the contact region between the electrode and the bladder. To limit heating of tissues which are disposed above the bladder, an upper portion 58 of the mesh structure may be masked off electrically from the energized mesh surface of the lower portion.

Figure 8A:
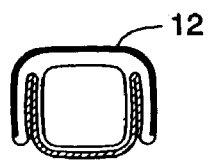
FIGS. 8A and 8B illustrate an alternative vaginal probe having a balloon deployable electrode for use in the method of FIG. 6.
Figure 8B:
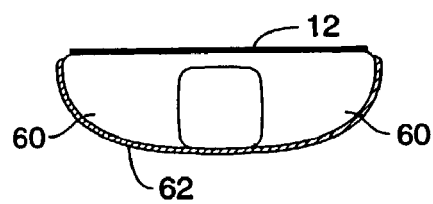

FIGS. 8A and 8B illustrate an optional deployable electrode support structure for use with vaginal probe 42. Electrode 12 can be collapsed into a narrow configuration for insertion and positioning within the vaginal cavity, as illustrated in FIG. 8A. Once electrode 12 is positioned adjacent to the target tissue, electrode 12 can be expanded by inflating lateral balloon 60 so that the deployed electrode assumes a substantially planar configuration. A cooling fluid may be recirculated through lateral balloon 60 to cool the electrode 12, and a thermally insulating layer 62 can help to minimize heat transfer from the adjacent tissues.

Figure 9:
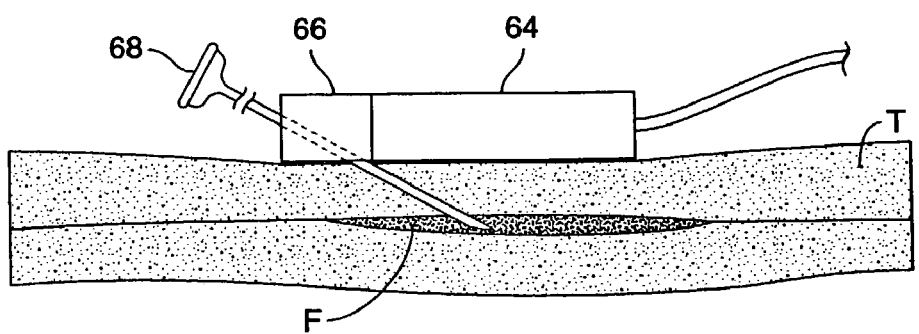
FIG. 9 is a cross-sectional view illustrating a structure and a method for ultrasonically positioning a temperature sensor within a target tissue.

Referring now to FIG. 9, the tissue shrinking system of the present invention may also include an ultrasonic transducer 64 for positioning one or both electrodes relative to fascia F. Transducer 64 will preferably include a transducer material such as PVDF (polyvinyladine fluoride) or PZT-5A (lead zirconate titanate). Transducer 64 may be incorporated into the probes of the present invention, thereby allowing the relative positions and angle between the electrode surfaces to be measured directly. Alternatively, transducer 64 may be positioned adjacent to fascia F, and a mark may be drawn upon the exposed skin (or other tissue surface) adjacent the fascia for subsequent positioning of a probe.

Transducer 64 optionally includes a needle guide 66. for insertion of a biopsy needle 68 through the view of the transducer and into the fascia. A thermocouple or other temperature sensing element may then be deployed in place of the biopsy needle.

Figure 10:
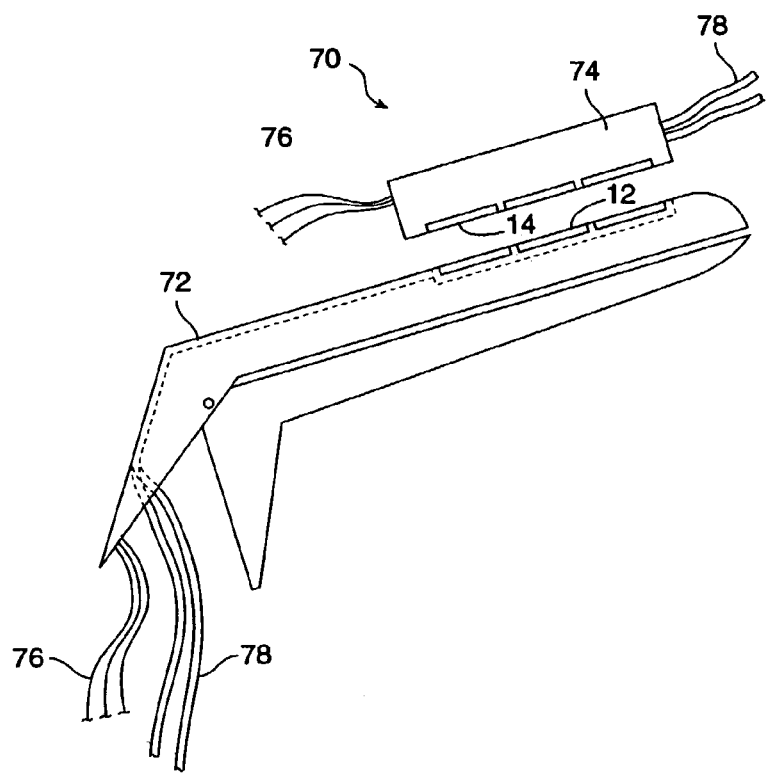
FIG. 10 illustrates an alternative system for selectively shrinking fascia through intermediate tissues, according to the principles of the present invention.

Referring now to FIG. 10, an alternative tissue shrinking system 70 includes an electrode 12 mounted on a speculum 72. Speculum 72 may be used to manually position electrode 12 within the vagina (or another body orifice), while an external applicator 74 is positioned against the skin to clamp the target tissue between electrode 14 and electrode 12. The speculum and external applicator 74 may be manually manipulated to clamp the target tissue between these structures, while electrical leads 76 and cooling fluid conduits 78 couple the probe and applicator to the remaining system components.

Figure 11:
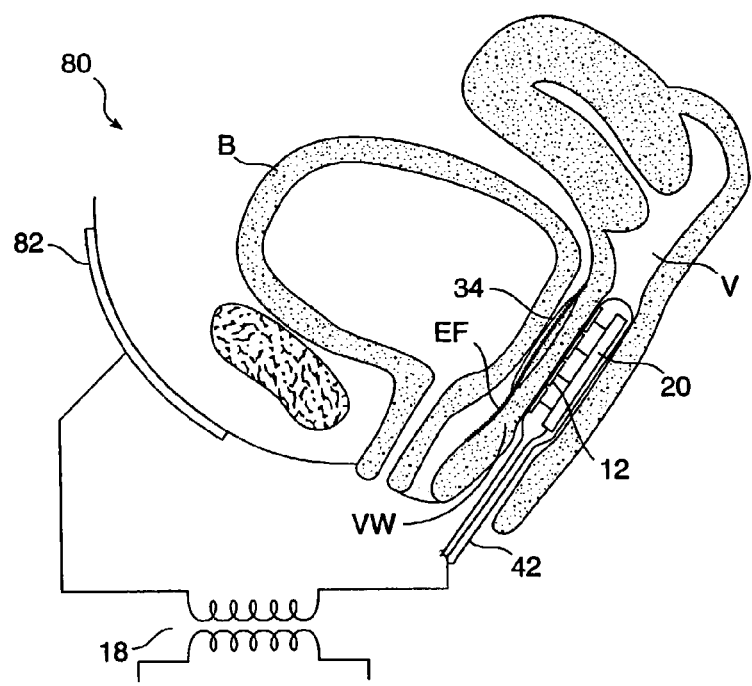
FIG. 11 schematically illustrates an alternative method for selectively shrinking endopelvic fascia using a vaginal probe having a cooled electrode array.

As described above regarding FIG. 2C, the use of bipolar electrodes of differing sizes allows the selective targeting of tissues. Specifically, heating will be concentrated near the smaller electrode surface. By using one electrode surface which is much larger than the other, the current density adjacent the large electrode will remain so low that little tissue heating is produced at that site, so that the very large electrode surface need not be cooled. FIG. 11 schematically illustrates a single probe heating system 80 which takes advantage of this mechanism to selectively heat fascia near a single probe.

In single probe system 80, offset target zone 34 is heated by RF energy selectively directed through the segments of electrode 12. The vaginal mucosa VM disposed between vaginal probe 42 and endopelvic fascia EF is protected by cooling the surface of electrode 12, as described above. Bladder B (and the other tissues opposite endopelvic fascia EF relative to vaginal probe 42) are heated significantly less than endopelvic fascia EF due to the divergence of the current as it travels away from electrode 12 and towards electrode pad 82, which may optionally be disposed on the abdomen, back, or thigh. Optionally, cooling water may be circulated through bladder B to further protect these tissues. Multiplexer 20 selectively energizes the electrode segments for differing amounts of time and/or with differing power to help tailor the temperature profile of offset target zone 34 about endopelvic fascia EF for selective uniform heating with minimal collateral damage. Various treatment regimes with alternating heating and cooling cycles can help to focus the heat therapy on the desired tissues. Multiplexer 20 may be disposed outside of the body in a proximal housing, in a separate control unit housing, or the like. The multiplexer can provide electrode segment drive control, optionally with switches for each electrode segment.

Figure 12:
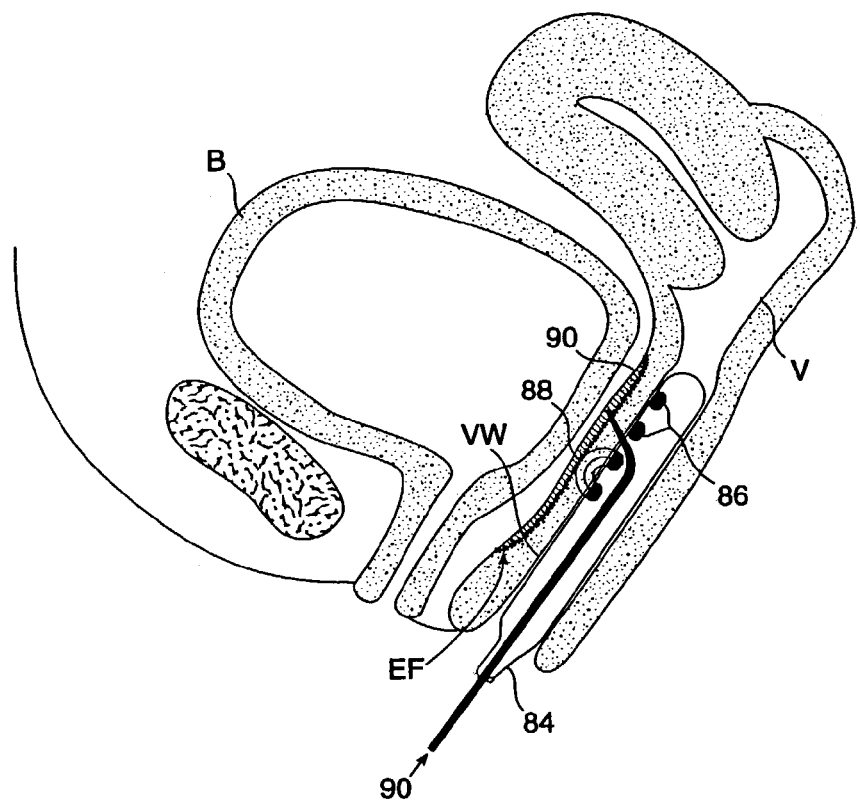
FIG. 12 schematically illustrates a cooled bipolar vaginal probe and a method for its use, the method including insulating a surface of the endopelvic fascia opposite the probe to limit the depth of heating.

Referring now to FIG. 12, a cooled bipolar probe 84 includes many of the structures and features described above, but here includes a series of bipolar electrodes 86. Bipolar electrodes 86 will preferably be cooled, and cooling surfaces may also be disposed between the separated electrodes. As more fully described in co-pending application Ser. No. 08/910,370, filed Aug. 13, 1997, bipolar electrodes 86 may optionally be formed as parallel cylindrical structures separated by a predetermined spacing to help direct a bipolar current flux 88 through tissue which lies within a particular treatment distance of probe 84.

The depth of penetration of the bipolar energy is controlled by the spacing and size of the electrode structures. The tissues distant from the cooled electrodes will be heated to a lesser extent than the tissues directly engaged by the electrodes, but will also be cooled to a lesser extent by the cooled electrodes and other cooling surfaces of bipolar probe 84. The tissues close to the electrodes will be heated to a greater extent, and will also be cooled more effectively. Therefore, a controlled regimen of timed pre-cooling and then heating is used to selectively raise the temperature of endopelvic fascia EF (or any other target tissue), while the vaginal mucosa adjacent probe 84 is protected by the cooled probe. Tissues at depths greater than the endopelvic fascia will generally be protected by the dissipation of bipolar current 88.

Since radiofrequency heating generally relies on conduction of electricity through the tissue, one additional mechanism for protecting the tissues at depths greater than the target area would be to inject an insulating fluid 90 into the space surrounding the vaginal wall on the far side of endopelvic fascia EF. Insulating fluid 90 may optionally comprise a gas such as $CO_2$, or may alternatively comprise a liquid such as isotonic Dextran™ in water. Insulating fluid 90 will electrically insulate the adjacent organs and prevent heating of tissues that might otherwise be in contact with the vaginal fascial outer lining. Insulating fluid 90 is here injected using a small needle incorporated into bipolar probe 84, the needle preferably being 22 ga or smaller.

Figure 13:
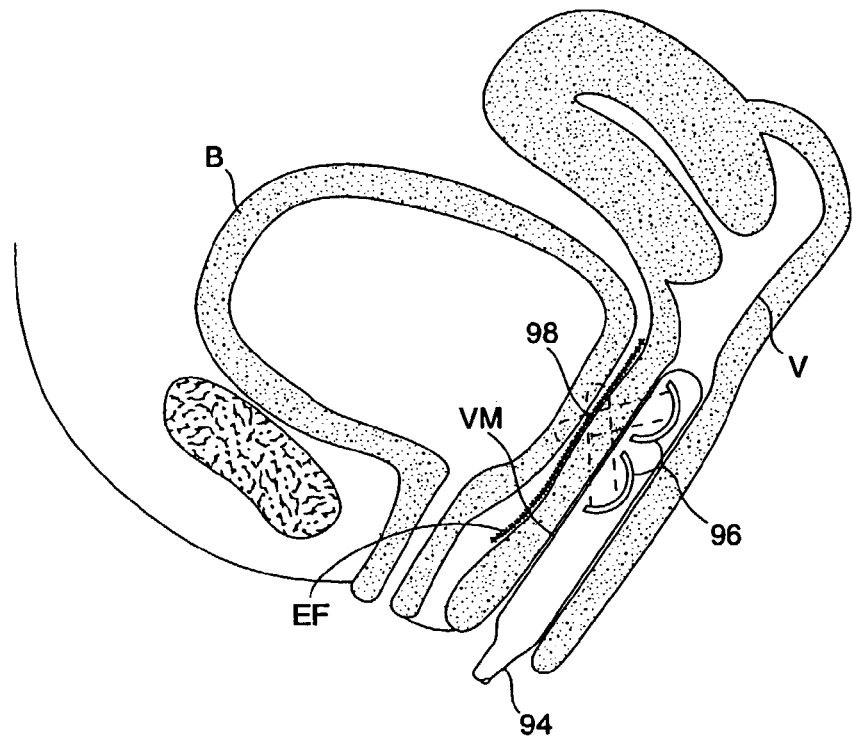
FIG. 13 schematically illustrates a method for selectively shrinking endopelvic fascia by transmitting microwave or ultrasound energy from a cooled vaginal probe.

Referring now to FIG. 13, microwave probe 94 includes microwave antennas 96 which direct microwave heating energy 98 through the vaginal mucosa VM and onto endopelvic fascia EF. Microwave probe 94 will again typically include a cooled probe surface to minimize damage to vaginal mucosa VM. The microwave may optionally be produced by a phased array microwave antenna to decrease heating next to the cold probe relative to the heating of endopelvic fascia EF, or a more conventional microwave antenna may be used.

Microwave power having a frequency of about 2250 MHz is most often used for heating. However, the use of extremely high frequency microwaves would permit constructive interference at the intersection of microwave energy streams by control of the microwave frequency, phase, and electrode spacing. Such constructive interference of microwaves may be used to enhance the heating of the target tissue relative to the heat produced in the intermediate tissue between microwave probe 94 and endopelvic fascia EF (in this example). Injection of an electrically insulating fluid, such as Dextran™, may be used to absorb microwave energy and protect tissues beyond the target zone. In some embodiments, injection of a liquid contrast medium might be used to enhance visualization of the treatment region, increasing the visibility and clarity of the vagina V, bladder B, the other adjacent organs, and the spaces therebetween. Such a contrast medium will typically be highly visible under ultrasonic or fluoroscopic imaging modalities.

An alternative form of energy which may be used in a probe schematically similar to that illustrated in FIG. 13 is ultrasonic heating. A cooled ultrasonic probe could be used to provide heating of the endopelvic fascia adjacent the vagina, preferably while protecting the adjacent tissues using a material which reflects ultrasound. Suitable protection materials include $CO_2$ or a liquid/foam emulsion material. High intensity ultrasound is able to heat tissues at a distance from the probe, and may be focused to apply the most intense heating at a particular treatment site. Concentration of ultrasound energy deep in the body may avoid heating of tissues at the entry site of the focused ultrasound beam, although gas pockets and bony structures may absorb and/or reflect the focused ultrasound energy, so that tissues may be damaged by both localized heating and cavitation. Once again, the surface of an ultrasound probe will typically be cooled to protect the tissues which are directly engaged by the probe.

Figure 14:
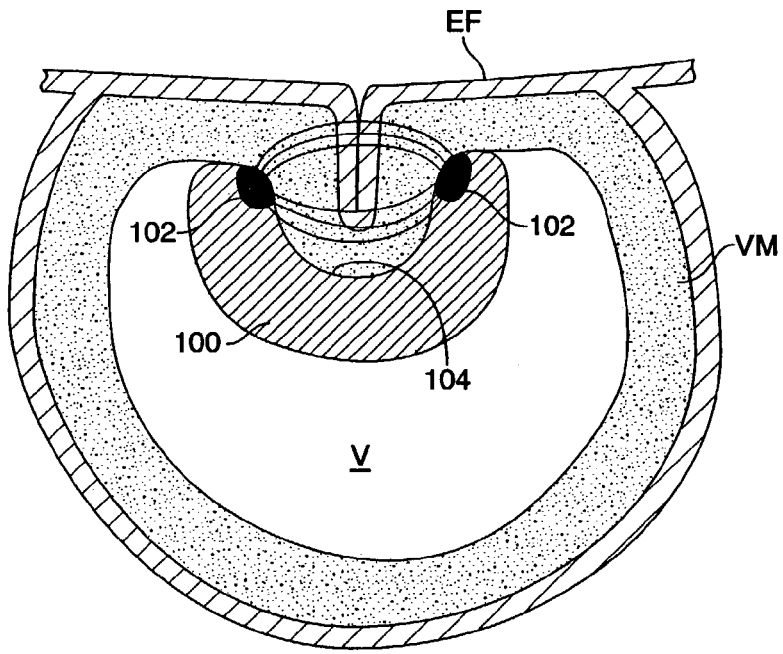
FIG. 14 is a cross-sectional view illustrating a method for selectively shrinking endopelvic fascia by grasping and folding the wall of the vagina or colon to facilitate focusing of heating upon the fascia, and to enhance shrinkage of the fascia by decreasing tension in the fascia while the fascia is heated, according to the principles of the present invention.
Figure 15:
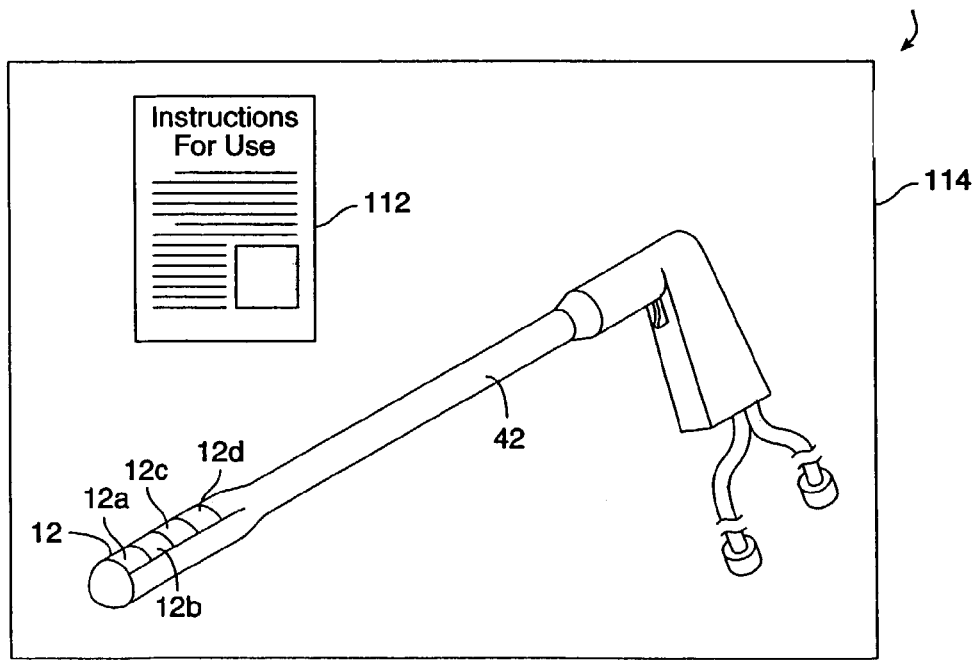
FIG. 15 is a schematic illustration of a kit including the vaginal probe of FIG. 5, together with instructions for its use to shrink tissues, according to the methods of the present invention.
Figure 16:
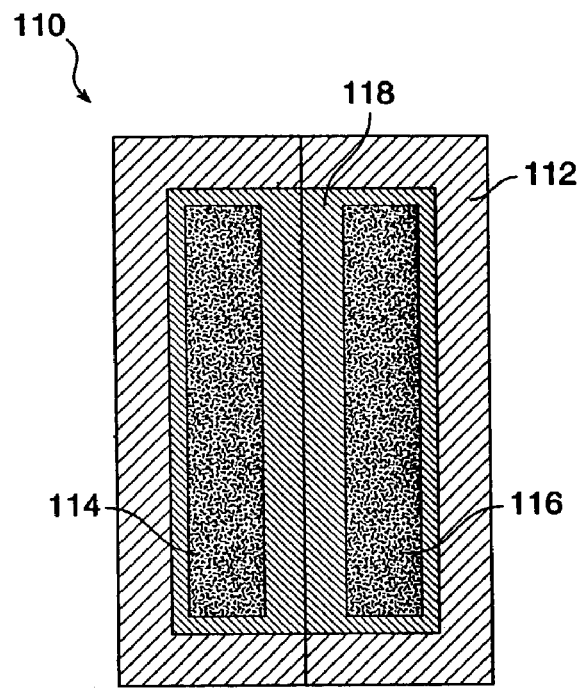
FIG. 16 illustrates an exemplary probe structure having two bipolar cooled electrode surfaces for heating a target tissue through an intervening tissue.
Figure 17:
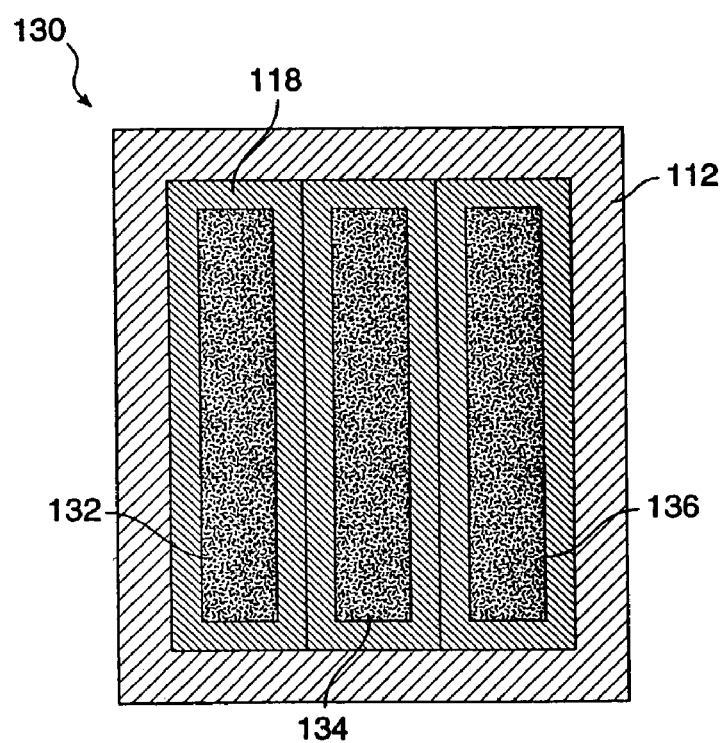
FIG. 17 illustrates an alternative exemplary probe structure similar to the probe of FIG. 16, having three alternating bipolar electrodes.

A cross-section of a grasping bipolar probe 100 is illustrated in FIG. 14. Grasping probe 100 grips and folds an anterior portion of the vaginal wall, including both the vaginal mucosa VM and endopelvic fascia EF, as shown. It should be understood that the targeted fascia may be separated from the probe by muscle, vasculature, and the like, as well as by vaginal mucosa VM. Endopelvic fascia EF is typically about 1 mm thick, while the grasped, folded vaginal wall will typically be between about 10 mm to 14 mm thick. The folded endopelvic fascia EF may thus be heated and contracted between cooled bipolar electrodes 102, as described above. Depending on the length of the fold, cooled bipolar electrodes 102 may optionally be formed as wide elongate plates. Grasping may be accomplished mechanically or by applying a vacuum to draw the vaginal wall into a cavity 104 of grasping probe 100. By drawing the endopelvic fascia into close proximity of both electrodes, a finer focusing of the heating may be accomplished, thereby minimizing the damage to adjacent tissues. Additionally, grasping probe 100 may draw the tissue inward to relieve any tension in the fascia, thereby enhance the shrinkage. As described above regarding FIG. 12, $CO_2$ or some other insulating medium may be used for additional protection of adjacent tissues and organs.

A kit 110 includes vaginal probe 42 and instructions 112 for use of the probe to shrink tissues, the probe and instructions disposed in packaging 114. The instructions may set forth the method steps for using probe 42 described hereinabove for selectively shrinking pelvic support tissues as a therapy for urinary incontinence, or may alternatively recite any of the other described methods. Additional elements for system 10 (see FIG. 1) may also be included in kit 110, or may be packaged separately.

Instructions 112 will often comprise printed material, and may be found in whole or in part on packaging 114. Alternatively, instructions 112 may be in the form of a recording disk or other computer-readable data, a video tape, a sound recording, or the like.

The present invention further encompasses methods for teaching the above-described methods by demonstrating the methods of the present invention on patients, animals, physical or computer models, and the like.

Exemplary cooled bipolar electrode structures having a protruding film are illustrated in more detail in FIGS. 16–19. A two electrode probe 110 is illustrated in a front view in FIG. 16. Two electrode probe has a probe body 112 supporting a first electrode 114 and a second electrode 116. An electrically insulating and thermally conducting film 118 extends along the electrode surfaces, covering the adjacent edges of the electrodes so as to prevent localized heating and charring of tissues when the electrodes are energized in a bipolar manner.

Figure 18:
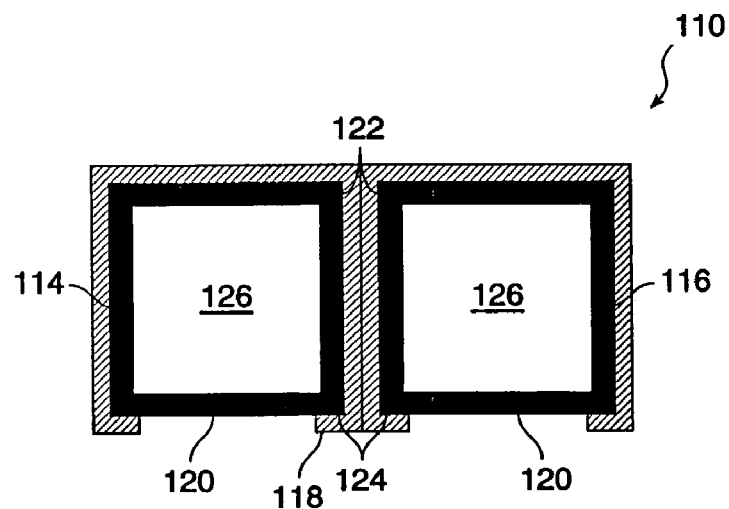
FIG. 18 is a cross-sectional view through the electrodes of FIG. 16.
Figure 19:
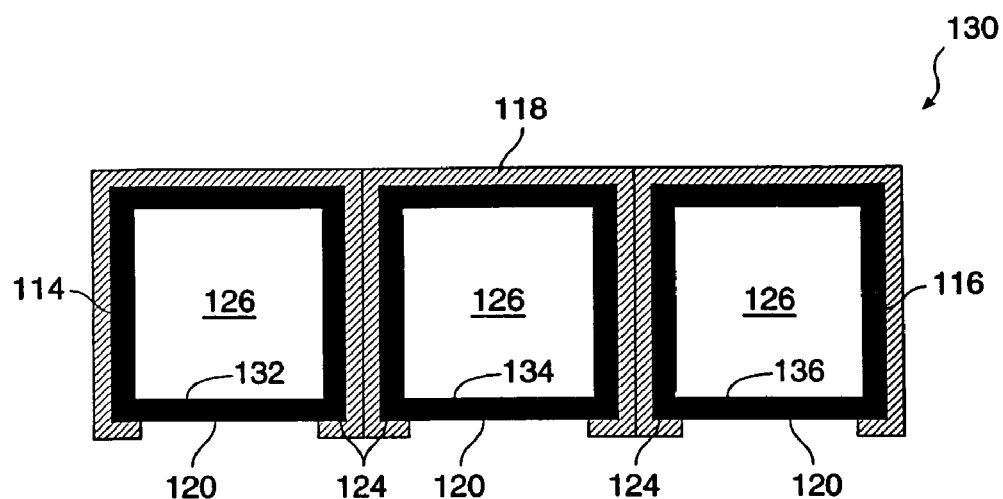
FIG. 19 is a cross-sectional view through the electrodes of FIG. 17.

The structure of electrodes 114, 116 can be seen in more detail in the cross-section of FIG. 18. The electrodes comprise electrically and thermally conductive materials, typically being formed as metal tubes, and ideally comprising stainless steel, brass, copper, steel, titanium, gold, or the like. Optionally, the exposed electrode surfaces of the electrode tubes may be coated with a thin film comprising a biocompatible material such as silver, or any of the other suitable materials listed above. Electrodes 114, 116 have electrode surface 120 and side surfaces 122 with an edge 124 therebetween. A cooling fluid 126 is disposed within the lumen of the electrode tubes, and may flow through the tubes either in series or in parallel, with the cooling fluid flow path optionally extending through probe body 112, and/or directly between the electrode tubes. Typical cooling fluids may comprise electrically conductive fluids such as chilled, physiological saline in separate fluid paths for the bipolar electrode pairs, but will preferably comprise a poor electrical conductor such as water and/or isotonic Dextran™ solution. The cooling fluid will typically be close to, but often above 0° C.

Film 118 will preferably be electrically insulating and thermally conducting so as to provide cooling along the exposed film surface between first and second electrodes 114, 116. Film 118 may comprise a variety of materials, such as Kapton™ tape, Mylar™ tape, a PTFE tape such as Teflon™, and anodization. Film 118 may be applied as a tape, a fluid (such as a paint or an adhesive), a plating, or the like, and will generally have sufficient thickness to act as an electrical insulator and a thermal conductor. Further alternative insulation film materials may comprise polyimide, spray-on ceramics, electroplated insulation, photoimageable polymers, epoxy, and urethanes. In the exemplary embodiment, the exposed electrode surfaces 120 have a width in a range from about 3 mm to 10 mm, while the exposed cooling surface of film 118 disposed between the electrodes also has a width in a range from about 3 mm to about 10 mm. The electrode need not be limited to a one or two dimensional array. In fact, electrode widths and separation may be easily varied along the axes of the tubes by applying film 118 over a curving area.

It should be noted that a wide variety of alternative electrode configurations might be used within the scope of the present invention. For example, a three electrode probe 130 includes three tubular electrodes 132, 134, 136 mounted in a plastic probe body 112, with electrodes and film structures substantially similar to those of FIGS. 16 and 18. It should be understood that electrode surfaces 120 need not be completely planer. For example, the exposed electrode surfaces may comprise portions of a large diameter cylinder as illustrated in co-pending PCT Application No. PCT/US98/16754, filed on Oct. 7, 1998, the full disclosure of which is incorporated herein by reference, or may comprise portions of a sphere. When more than two electrodes are provided, they may be energized either simultaneously or sequentially as bipolar pairs. Once again, a wide variety of electrode geometries and treatment cycles might be used.

Figure 20A:
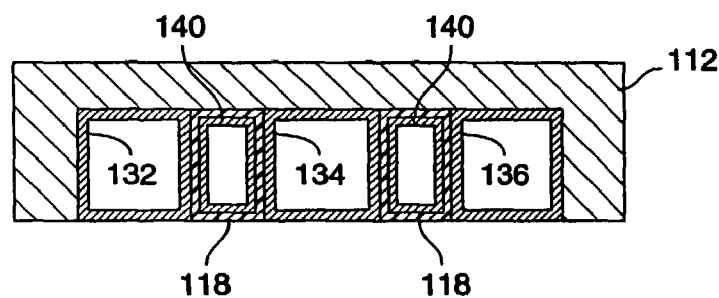
FIGS. 20A–C illustrate further alternative cooled bipolar probe structures.
Figure 20B:
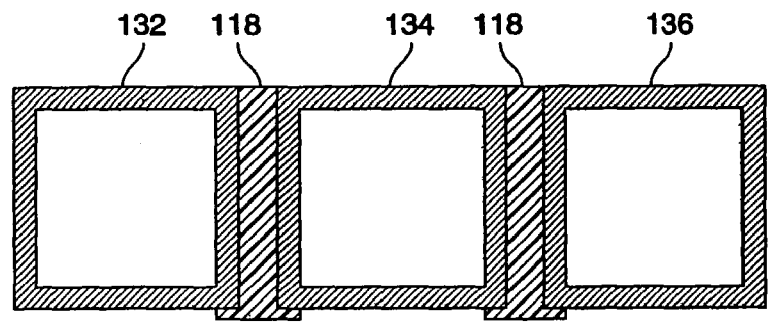
Figure 20C:
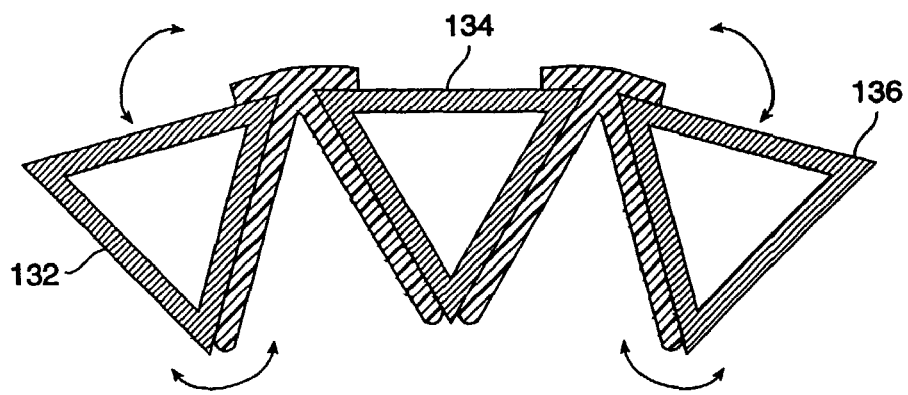

Still further related cooled probe structures are illustrated in FIGS. 20A–C. In the embodiment of FIG. 20A, film 118 isolates cooling fluid path tubes 140 electrically, and allows contiguous cooling across separated bipolar electrodes. This and other probe structures having three or more electrodes will often be multiplexed by driving bipolar current between, for example, electrodes 132 and 134, and then between electrodes 134 and 136. Cooling tubes 140 are electrically insulated, and can be allowed to float with respect to electrodes 132, 134, and 136.

Several factors will alter the heating depth profile for the bipolar probes of the present invention. First, the width of the insulation provided by film 118 between the exposed electrodes is related to the maximum treatment depth. Second, both the width of the active exposed electrodes and the width of the electrically insulated separation distance between the electrodes determine the maximum depth of the intervening tissue which can be thermally cooled and effectively protected while treating the target tissue. Third, reducing the separation gap between electrodes will eventually result in localized hot spots at the surface of the inside edges of the powered electrodes. The minimum interelectrode separation can be decreased by multiplexing or alternating the bipolar power between three or more electrodes as described above. An electrically insulating film extends to, and preferably over and beyond the electrode edge, and/or a protruding insulating rib may also reduce localized hot spots.

Still further alternative electrode tube/film structures are illustrated in FIGS. 20B and C. The embodiment of FIG. 20C includes electrode tubes which define acute angles between the electrode and side surfaces. Film 118 here acts as a living hinge between the electrodes, allowing the probe to conform to a curving tissue surface such as a lumenal wall. The acute tube angles increase the range of flexibility of the probe, and similar probes may be used having cooling tubes between active electrodes, a combination of different electrode tube shapes, or the like.

While the exemplary embodiments have been described in some detail, by way of example and for clarity of understanding, a variety of modifications, adaptations, and changes will be obvious to those who skill in the art. Therefore, the scope of the present invention is limited solely by the appended claims.

What is claimed is:

1. A probe comprising:
    a probe body;
    a first electrode coupled to the probe body and having a first electrode surface with a first edge;
    a second electrode coupled to the probe body and having a second electrode surface with a second electrode edge adjacent the first edge, the first and second surfaces fixed relative to each other and aligned to simultaneously engage a tissue surface; and
    an insulator disposed between the first and second electrodes, the insulator extending beyond the first and second edges so as to avoid edge induced concentration of current flux.

2. The probe as claimed in claim 1 wherein the insulator comprises an electrically insulating and thermally conductive film.

3. The probe as claimed in claim 1 wherein the insulator comprises a surface area that is smaller than a surface area of the first electrode surface and/or the second electrode surface.

4. The probe as claimed in claim 1 further comprising a biocompatible material disposed over each of the first electrode surface and second electrode surface.

5. The probe as claimed in claim 1 wherein the first electrode surface and second electrode surface are substantially parallel to each other and on a same plane.

6. A probe as claimed in claim 1 further comprising an electrosurgical power source that transmits bipolar electrosurgical power between the first and second electrodes.

7. A bipolar probe comprising:
    a first electrically and thermally conductive tube having an electrode surface and a side surface with an edge therebetween;
    a second electrically and thermally conductive tube having an electrode surface and a side surface with an edge therebetween;
    a thin film comprising a biocompatible material over each of the electrode surfaces of the first conductive tube and second conductive tube; and
    an electrical insulation film disposed between the side surfaces of the tubes, the film being electrically insulating and thermally conductive and having an exposed cooling surface extending between and over the edges and along a portion of the electrode surfaces of the first and second tubes, the cooling surface being thermally coupled to a cooling fluid.

8. A probe as claimed in claim 7 further comprising a thermally conductive cooling tube disposed between the first and second tubes, the electrical insulating and thermally conductive film being disposed over the cooling tube and the cooling fluid being disposed in the first and second tubes and the cooling tube.

9. A probe as claimed in claim 7, wherein the electrode surfaces have exposed widths in a range from about 3 to about 10 mm, and wherein the cooling surface of the electrical insulating and thermally conductive film has a width in a range from about 3 to about 10 mm.

10. A probe as claimed in claim 7, wherein the electrode surfaces and the side surfaces define acute angles at the edges, the electrical insulating and thermally conductive film flexing to act as a living hinge coupling the first and second tubes.

11. A probe as claimed in claim 7, further comprising a bipolar electrical connector coupled to the first and second tubes by first and second electrical conductors, the electrically insulating and thermally conductive film electrically isolates the sides of the tubes.

12. A bipolar probe comprising:
    at least one cooling fluid path;
    cooling fluid flowing within the at least one fluid path;
    a first electrode thermally coupled to the cooling fluid within the at least one fluid path;
    a second electrode thermally coupled to the cooling fluid within the at least one fluid path;

a thin film of biocompatible material disposed over each of the first electrode and the second electrode; and a cooling surface extending between the first and second electrodes, the cooling surface being thermally coupled to the cooling fluid within the at least one fluid path so as to cool a contiguous tissue surface engaged by the electrodes and the cooling surface while a bipolar current between the electrodes heats a target tissue disposed at a distance from the target surface.

13. The bipolar probe of claim 12 wherein the cooling surface comprises a surface area that is smaller than a surface area of the first electrode or the second electrode.

14. The bipolar probe of claim 12 further comprising an electrosurgical power sauce that transmits bipolar electrosurgical power between the first and second electrodes.

15. The bipolar probe of claim 14 further comprising a multiplexer coupling the first and second electrodes to the electrosurgical power source, the multiplexer sequentially energizing the first and second electrodes so as to heat a target tissue separated from the first and second electrodes by an intermediate tissue while the cooling surface reduces injury to the intermediate tissue.

16. A probe comprising:

a first electrode having a first electrode surface with a first edge;

a second electrode having a second electrode surface with a second edge adjacent the first edge, the first and second surfaces aligned to simultaneously engage a tissue surface;

a thin film of biocompatible material disposed over each of the first electrode surface and the second electrode surface; and an electrically insulating and thermally conductive layer disposed between the first and second electrodes, the electrically insulating and thermally conductive layer extends beyond the edges so as to avoid edge induced concentration of current flux, wherein the electrically insulating and thermally conductive layer is coupled to a cooling system.

17. A probe as claimed in claim 16 wherein the electrically insulating and thermally conductive layer comprises a protruding rib.

18. A probe as claimed in claim 16 wherein the electrically insulating and thermally conductive layer comprises a film.

* * * * *